United States Patent [19]

Forgione et al.

[11] 4,375,972

[45] Mar. 8, 1983

[54] HETEROGENEOUS CHEMILUMINESCENT IMMUNOASSAYS UTILIZING METALLO PORPHYRIN TAG

[75] Inventors: Peter S. Forgione; William A. Henderson, Jr., both of Stamford, Conn.

[73] Assignee: Allied Corporation, Morris Township, Morris County, N.J.

[21] Appl. No.: 328,007

[22] Filed: Dec. 7, 1981

Related U.S. Application Data

[62] Division of Ser. No. 85,601, Oct. 17, 1979, abandoned.

[51] Int. Cl.³ .................... G01N 33/54; G01N 33/58; G01N 21/76
[52] U.S. Cl. ..................................... 436/531; 436/546
[58] Field of Search ..................... 23/230 B; 424/8, 12

[56] References Cited

U.S. PATENT DOCUMENTS

| | | | |
|---|---|---|---|
| 3,797,999 | 3/1974 | Witz | 23/230 B |
| 4,104,029 | 8/1978 | Maier | 23/230 B |
| 4,160,645 | 7/1979 | Ullman | 23/230 B |
| 4,205,952 | 6/1980 | Cais | 23/230 B |
| 4,230,664 | 10/1980 | Cais | 23/230 B |
| 4,238,195 | 12/1980 | Boguslaski | 23/230 B |
| 4,293,310 | 10/1981 | Weber | 23/230 B |
| 4,318,707 | 3/1982 | Litman | 23/230 B |

*Primary Examiner*—Sidney Marantz
*Attorney, Agent, or Firm*—Webb, Burden, Robinson & Webb

[57] ABSTRACT

A conjugate for use in the detection and quantification of antibodies and antigens in body fluids by immunoassay procedures and chemiluminescent immunoassay procedures utilizing the conjugate. The conjugate is capable of reacting with an antigen or an antibody or both and includes a tag capable of catalyzing a chemiluminescent reaction. The conjugate may be an antibody or an antigen to which a metallo porphyrin tag is attached and preferably comprises immunoglobulin to which hemoglobin is attached.

9 Claims, No Drawings

HETEROGENEOUS CHEMILUMINESCENT IMMUNOASSAYS UTILIZING METALLO PORPHYRIN TAG

This application is a division of application Ser. No. 085,601, filed Oct. 17, 1979, now abandoned.

FIELD OF INVENTION

This invention relates to the field of immunoassay techniques for the detection and quantification of antibodies and antigens (including haptens) and other substances present in small amounts in body fluids. More specifically, it relates to chemiluminescent immunoassay procedures and a novel conjugate for use in those procedures.

DESCRIPTION OF THE PRIOR ART

Various test systems have been developed for the detection and quantification of antibodies, antigens and other substances present in small amounts of body fluids. The most sensitive are immunoassay procedures which take advantage of the fact that an antibody binds specifically to its antigen and the reaction obeys the mass action law, $Ab + Ag \rightleftharpoons AbAg$.

Several immunoassay techniques are currently employed which can be classified by their binding characteristics. The most common utilize competitive and sandwich binding. Regardless of the technique a conjugate tagged for detection must be employed. The most widely used tags are radioisotopes and the procedure is called radioimmunoassay (RIA). Other procedures using different tags include enzyme immunoassay (EIA) and fluorescent immunoassay (FIA).

Radioimmunoassays using as tags the radioactive isotopes $^{125}I$, $^{14}C$ or $^3H$ presently command the major share of the market because of their extremely high sensitivities, that is, their ability to detect $10^{-15}$ moles or less of antigen or antibody. Despite their high sensitivity, RIA's suffer from the following disadvantages: (1) the beta and gamma counters required for the readout system are expensive and require expensive upkeep by highly trained service persons, (2) supervisory personnel must be highly trained and licensed by the government for work with radioisotopes, (3) because of the radioactivity RIA's are effectively prohibited in many countries outside of the United States, (4) the high radioactivity required for an appropriate signal requires the use of short-lived isotopes, thus requiring the frequent resynthesis of tagged compounds, and (5) the short lives means that the signal to concentration of tag ratio is continually and rapidly changing requiring frequent recalibration for each assay.

Enzyme immunoassays require the use of complex biological materials with retention of their native activity. The procedures themselves are time consuming due to the slow nature of the readout reaction and do not always yield requisite high sensitivities.

Fluorescent systems have slightly lower sensitivity limits than radioimmunoassay systems and require long incubation periods. In addition, high and variable blanks are often encountered.

Chemiluminescence refers to light produced as a direct result of chemical change. It involves the transformation of the free energy of a chemical reaction into light energy. The chemical reaction must release sufficient energy to populate an excited energy state; the reaction pathway must favor the formation of the excited state product; and the excited state product must be capable of emitting a photon itself for transferring its energy to another molecule that can emit.

A well-known, highly efficient chemiluminescent reaction is the oxidation of luminol (5-amino-2,3-dihydrophthalazine-1,4-dione) in a basic solution. The most frequently used oxidant is hydrogen peroxide in the presence of a catalyst such as $Fe(CN)_6^{-3}$, $Cu(II)$, and $Co(II)$. Other oxidants include perborate, hypochlorite, iodine, permanganate and oxygen.

Chemiluminescence has been utilized in immunoassay procedures. Maier U.S. Pat. No. 4,104,029 discloses a procedure for the assay of pharmacologically, immunologically and biochemically active compounds in biological fluids in which a ligand is labeled with a chemiluminescent material such as luminol. In addition, it is known that iron and specifically iron protoporphyrin compounds react with luminol in the presence of hydrogen peroxide or sodium perborate and a base to give an excited species which emits light with high efficiency, see Ewetz and Thore's Factors Affecting the Specificity of the Luminol Reaction with Hematin Compounds, *nalytical Biochemistry*, 71, 564–570 (1976).

SUMMARY OF THE INVENTION

This invention provides a fast, sensitive and objective immunoassay for antigens or antibodies. It eliminates the radioisotope hazards and the need for highly trained personnel. It further eliminates the need for special facilities associated with isotope work. In addition, it utilizes only simple instrumentation and provides fast readout and high sensitivity (up to $10^{-15}$ mole detection). The invention provides a long-lived tagged immunoreagent which is of relatively low cost and of ready availability. Because of its universal reactivity, it is applicable to a number of different assay procedures.

The invention is directed to a conjugate for use in an immunoassay procedure which is detectable by chemiluminescence. The conjugate comprises an immunologically active compound to which a metallo porphyrin tag is attached. Any antibody or binding partner for an antibody including antigens and haptens may be used. Antibodies raised in animal species such as goats and rabbits are particularly suitable. Antigens such as hormones and blood plasma proteins and haptens are suitable. Immunoglobulin and particularly IgG is particularly useful because of its availability and because it acts as both an antigen and antibody. Antigens which naturally contain iron porphyrin such as hemoglobin, myoglobin and cytochrome C may be used as the entire conjugate.

Because the tag functions as a catalyst rather than a reactant, each tag produces a plurality of photons whereas a luminol tag would only produce a single photon. This results in two advantages, namely greater sensitivity and prolonged emission.

The metallo porphyrin tag may be a molecule containing a metallo porphyrin and particularly a protein containing iron porphyrin. It may be iron porphyrin itself such as hemin. Hemoglobin, myoglobin, cytochrome C and catalase are suitable.

The metallo porphyrin tag is attached to the antigen or antibody by means of known bifunctional linking agents such as cyanuric chloride, acrylyl chloride, and glutaraldehyde.

The conjugate is useful in various immunoassay procedures to determine the concentration of an unknown in an analyte. Typically such procedures use a reagent, an analyte and a conjugate. In a competitive assay the reagent which is generally attached to a solid phase such as nylon or polystyrene must be a binding partner for the conjugate. The analyte may be a binding partner for the conjugate or the reagent but not both. In a sandwich type assay the conjugate and the reagent cannot be binding partners for each other. Both are binding partners for the analyte. The binding reactions can be shown graphically as follows:

A. Competitive Assay

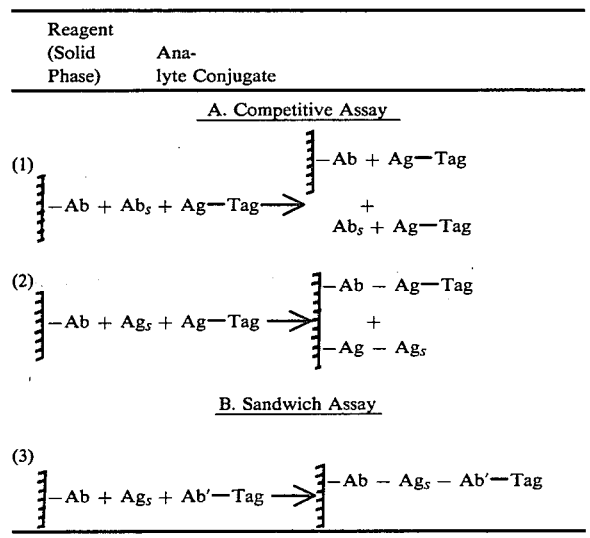

Thus in a competitive assay the greater the amount of the unknown ($Ab_s$ or $Ag_s$) in the analyte, the less conjugate which can react with the reagent. In a sandwich assay the opposite is true. As the amount of the unknown in the analyte increases the amount of conjugate which reacts with the reagent increases.

To determine the amount of the unknown in the analyte, the reagent is separated from the remaining reactants. It is for ease in separation that the reagent is generally attached to a solid phase. After separation including thorough washing to make certain no unreacted conjugate remains, the reagent is mixed with a chemiluminescent reactant. Luminol is preferred because of its efficiency. Other chemiluminescent substances which may be used include tetrabis (dimethylamino) ethylene, luciferin, lucigenin (dimethyl diacridinum nitrate) and oxalyl chloride. As an oxidant sodium perborate is preferred. However, other known catalysts may be used.

The metallic component of the tag in the conjugate will catalyze the chemiluminescent reaction. The amount of light emission recorded in a standard manner gives a quantitative determination of the amount of conjugate which is bound to the reagent and, hence, the amount of unknown in the analyte.

DESCRIPTION OF THE PREFERRED EMBODIMENTS

The following examples serve to illustrate the practice of the invention but are not to be regarded as limiting:

EXAMPLE I

Competitive Assay of Human Immunoglobulin G

A. Preparation of Reagent (Solid Phase)

Nylon mesh was partially hydrolyzed by treating in 2 N HCl at 37° overnight. The nylon was washed free of acid with 0.01 M $Na_2CO_3$, pH 10, and washed with water. The nylon was placed in a solution of 400 mg of 1 ethyl-3 (3-dimethylaminopropyl)-carbodiimide in water, pH 3.7. The pH was maintained between 3.5 and 3.8. The activation reaction was continued at room temperature until the consumption of acid ceased. The nylon was rapidly washed two times with dilute HCl (pH 3.4 to 3.8).

Human immunoglobulin, dissolved in 50 mM NaCl, pH 3.4, to 10 mg of protein per ml, was added to the washed activated nylon and the pH was gradually raised to pH 7 over 60 minutes. The attachment reaction was allowed to proceed for 60 minutes at pH 7. The pH was adjusted to 7.2 to 7.4 and the composition was incubated for 4 hours.

The nylon was washed according to the following sequence: 2 M NaCl, two times; water; 10 mM phosphate buffer, pH 7.35, containing 0.3 M NaCl, 0.2% bovine serum albumin and 0.1% Tween 80, two times; phosphate buffered saline, two times; and water. The washed nylon-immunoglobulin reagent was air dried and used in 1 $cm^2$ pieces as the solid phase in immunoassays.

B. Preparation of Conjugate

An iron porphyrin-antibody conjugate was prepared as follows: Goat anti-human serum was partially purified by precipitation with ammonium sulfate, and dialyzed against saline. To 2 ml of this solution (100 mg protein), 30 mg of sodium bicarbonate and 2 ml of water was added. A solution of cyanuric chloride in dioxane, 4 mg/ml, was added to the rapidly stirring solution of globulin. After 2 minutes a solution of 100 mg of hemoglobin in 4 ml of water was added and the binding reaction was allowed to proceed for 18 hours at 25° C.

After reaction, the mixture was charged onto a 1.5×100 cm column of polyacrylamide gel, Bio-Gel P-200 (100–200 mesh) and elution performed with 0.002 N phosphate buffer, pH 7.0, containing 0.05 M sodium chloride and 0.02% sodium azide. In this way any unreacted hemoglobin could be removed from the conjugate. The fractions containing both hemoglobin and antibody activity were pooled and used as the conjugate.

C. Preparation of Chemiluminescent Reactants

The chemiluminescent readout measurements were performed on an Aminco Chem-Glo Photometer.

The following solutions were used for CL analyses:

Luminol Stock Solution. To 2.00 mg of luminol and 32 mg of glucose was added 4 ml of 0.1 N sodium hydroxide. After complete dissolution of the luminol, the solution was made up to 100 ml with water. The solution was stored at 4°.

Luminol Working Solution. Each working day, 1.00 ml of the above solution and 10 ml of 0.1 N sodium hydroxide was made up to 100 ml with water.

Perborate Solution. Each working day, 77 mg of sodium perborate was dissolved in 100 ml of water.

Analyses of chemiluminescence were carried out as follows:

In a shell vial was placed 0.5 ml of the test solution, made up in the luminol stock solution as described above. This was placed in the sample compartment of the Chem-Glo Meter. To this was then added 0.1 ml of the perborate solution. The light output was taken as the maximum pen deflection shown on the recorder. In most cases, an average of the results of three sample injections was used.

D. Assay Procedure

An immunoassay was performed with the human immunoglobulin-nylon solid phase and the iron porphyrin-antibody conjugate.

Nylon discs (surface area = 1 sq. cm.) were incubated with 0.4 ml of conjugate at various dilutions plus 0.1 ml of phosphate buffered saline or 0.4 ml of conjugate at various dilutions plus 0.1 ml of a solution of human immunoglobulin. All dilutions of conjugate and human immunoglobulin were made with phosphate buffered saline. After incubation for 60 minutes at room temperature, the solutions were aspirated and the nylon discs were washed successively with 4.5 ml of 0.5% BSA-0.05% Tween 20, 2 M NaCl-pH 9.0, BSA-Tween-20 and two times with 0.01 M phosphate pH 6.1 buffer.

After washing, individual discs were eluted with a luminol working solution. For this purpose, 3.0 ml of the luminol working solution was added to each tube and the tube plus contents was sonicated for five minutes. A 500 μl aliquot of the solution was introduced into a vial, placed in an appropriate instrument such as the Aminco Chem-Glo Photometer, reacted with a solution of sodium perborate and the resultant light output was recorded.

E. Results

The results obtained are presented in Table I. Inhibition of conjugate uptake onto the insoluble nylon-human immunoglobulin is seen over a wide range of conjugate concentration and competing immunoglobulin concentrations.

TABLE I

| Nylon Sheet | Conjugate Conc. (mg/ml) | Soluble Immunoglobulin Added (μg) | Relative Light Intensity |
| --- | --- | --- | --- |
| #A | 0.1 | 0 | 4,300 |
| B | 0.1 | 0.1 | 2,885 |
| C | 0.04 | 0 | 1,995 |
| D | 0.04 | 0.1 | 1,245 |
| E | 0.04 | 100.0 | 202 |
| F | 0.02 | 0 | 1,490 |
| G | 0.02 | 0.1 | 364 |
| H | 0.01 | 0 | 1,125 |

TABLE I-continued

| Nylon Sheet | Conjugate Conc. (mg/ml) | Soluble Immunoglobulin Added (μg) | Relative Light Intensity |
| --- | --- | --- | --- |
| I | 0.01 | 0.1 | 182 |
| J | 0.000 | 0 | 52 |

EXAMPLE II

Preparation of Hemoglobin-Antibody Conjugates

A series of hemoglobin-antibody conjugates were prepared as shown in Table II.

TABLE II

| | Activation Step | | | | Binding Step | Product Composition |
| --- | --- | --- | --- | --- | --- | --- |
| Example | Volume ml | Cyanuric Chloride mg | Time sec. | Temp. °C. | Hemoglobin mg | Hemoglobin$^a$ Innumoglobulin |
| II-A | 4 | 4 | 120 | 25 | 400 | 0.83 |
| B | 4 | 8 | 120 | 25 | 400 | 0.65 |
| C | 4 | 4 | 120 | 25 | 100 | 0.63 |
| D | 4 | 4 | 600 | 25 | 100 | 0.74 |
| E | 4 | 8 | 120 | 25 | 100 | Insoluble products |
| F | 4 | 2 | 120 | 25 | 100 | 0.49 |
| G | 4 | 1 | 120 | 25 | 100 | 0.19 |
| H | 10 | 4 | 10 | 0 | 100 | 1.34 |
| I | 10 | 4 | 1 | 0 | 100 | 1.07 |
| J | 10 | 2 | 10 | 0 | 100 | 0.90 |
| K | 20 | 4 | 10 | 0 | 100 | 1.05 |
| L | 4 | 4 | 10 | 0 | 100 | 1.73 |

Conjugates were tested and had both CL catalyzing and immunological properties. Results similar to Example I were obtained in the immunoassay with conjugates II-C and II-L and nylon bound antibody from Example I.

EXAMPLE III

Competitive Assay of Immunoglobulins in Human Serum

Nylon bound human immunoglobulin, as prepared in Example I, and Hemogloblin conjugated to anti-immunoglobulin, Example II-C, were incubated in the presence and absence of human serum. Reduced light output was observed in the presence of human serum.

EXAMPLE IV

Direct Assay of Human Hemoglobin

Antibody to human hemoglobin was partially purified by ammonium sulfate precipitation; dissolved to 12 μg protein/ml of 0.05 M sodium carbonate, pH 9.6. The antibody was adsorbed onto polystyrene tubes (Falcon Number 2054) for 1 hour at 37° C. The solid phase antibody tubes were treated with 0.5% bovine serum albumin for 30 minutes at 37° C. and washed 2 times with 0.2% bovine serum albumin containing 0.5% Tween in buffered saline. The antibody tubes were incubated in the absence and in the presence of human hemoglobin for 30 minutes at room temperature and washed with the albumin-Tween buffered saline 3 times and chemiluminescence was measured as in Example I. Light emission was higher when hemoglobin was added to the tubes and proportional to the amount of hemoglobin present.

EXAMPLE V

Immunoassay of Myoglobin

Antibody to myoglobin was adsorbed to polystyrene and immunoassays were performed as in Example IV with similar results.

EXAMPLE VI

Sandwich Assay of Chorionic Gonadotropin

A. Preparation of Reagent

Goat antibody to human chorionic gonadotropin (HCG) bound to nylon beads: Partial hydrolysis of the nylon was accomplished with N HCL for 2 hours. The beads were washed and additional carboxyl groups were introduced by allowing the beads to react with an excess of maleic anhydride at a constant pH between pH 8 and 9 for 1 hour. The beads were washed and the carboxyl groups were activated with 2 g of water soluble carbodiimide at a constant pH of 4.5 to 5.2 for 30 minutes. Excess carbodiimide was removed and goat anti-HCG was bound to the beads for 3 hours at room temperature followed by 18 hours at 4° C. The antibody beads were treated with 0.2% bovine serum albumin in buffered saline, washed and stored in bovine serum albumin in buffered saline at 4° C. prior to use.

B. Preparation of Conjugate

An iron porphyrin containing peptide derived from cytochrome C was prepared by pepsin digestion of cytochrome C, followed by acid precipitation and dialysis. This peptide, demonstrated a higher chemiluminescent yield per porphyrin molecule than cytochrome C itself. Goat antibody to HCG was partially purified by ammonium sulfate precipitation and digested with pepsin to produce (Fab')$_2$ fragments which were purified by gel filtration on Sephadex G-75 column. Thiol groups were introduced onto the antibody fragment using N-acetylhomocysteine thiolactone and the thiolated antibody fragment was separated from excess thiolating reagent by gel filtration over a Sephadex G-25 column. The iron porphyrin peptide was activated for conjugation to the thiolated antibody fragment by introduction of maleimide moieties using m-maleimidobenzoyl N-hydroxysuccinimide ester followed by Sephadex G-25 filtration. The conjugate was prepared by mixing thiolated antibody fragment and maleimido-iron porphyrin peptide for one hour at room temperature followed by gel filtration on a Sephadex G-75 column.

Immunoassays using antibody to HCG bound to nylon beads and iron porphyrin conjugated to antibody fragments derived from antibody to HCG were performed.

C. Assay Procedure

Nylon beads conjugated with antihuman IgG were placed in glass tubes and incubated 30 minutes at 37° C. with 2.5 I.U. of HCG in a solution of 0.2% bovine serum albumin in phosphate buffered saline or phosphate buffered saline alone. The solutions were then aspirated and the beads were washed with 0.05 M HEPES, 0.15 M NaCl, pH 7.2 and then incubated for 30 minutes at 37° C. with various dilutions of the conjugate in 0.05 M HEPES, 0.15 M NaCl, pH 7.2 buffer. After incubation at 37° C. for 30 minutes, the beads were once again washed and the beads were eluted with 0.5 ml of 0.1% sodium dodecyl sulfate for five minutes. Luminol was added and light emission was measured as in Example I. Table VI shows results typical of this double antibody sandwich assay for an antigen.

TABLE IV

| Tube | HCG Added | Dilution of Conjugate | Relative Light Sensitivity |
|------|-----------|----------------------|---------------------------|
| 1 | + | 1:5 | 61.1 |
| 2 | + | 1:10 | 39.0 |
| 3 | + | 1:25 | 16.1 |
| 4 | + | 1:50 | 3.25 |
| 5 | + | 1:100 | 2.40 |
| 6 | + | — | 1.21 |
| 7 | — | 1:5 | 19.5 |
| 8 | — | 1:10 | 4.81 |
| 9 | — | 1:25 | 3.56 |
| 10 | — | 1:50 | 2.34 |
| 11 | — | 1:100 | 2.21 |
| 12 | — | — | 1.63 |

The data shows increased CL indicating increased uptake of conjugate in the presence of HCG over a wide range of conjugate dilutions.

I claim:

1. A heterogeneous immunoassay method for detecting or determining a suspected immunologically active substance in a sample comprising:
    (a) contacting said sample with a conjugate comprising an immunologically active compound having a metallo porphyrin tag, said conjugate forming a complex with the substance being assayed;
    (b) contacting the complex resulting from (a) with a chemiluminescent reactant; and
    (c) measuring the amount of light resulting from (b).

2. The immunoassay method of claim 1 wherein said immunologically active compound is an antibody or a binding partner for an antibody.

3. The immunoassay method of claim 1 wherein said metallo porphyrin is iron porphyrin.

4. The immunoassay method of claim 3 wherein said immunologically active compound is an antigen.

5. The immunoassay method of claim 3 wherein said iron porphyrin is derived from hemoglobin or myoglobin.

6. The immunoassay method of claim 3 wherein said iron porphyrin is derived from cytochrome C.

7. The immunoassay method of claim 3 wherein said immunologically active compound is a protein.

8. The immunoassay method of claim 7 wherein said protein is immunoglobulin.

9. The immunoassay method of claim 7 wherein said protein is a hormone.

* * * * *

UNITED STATES PATENT AND TRADEMARK OFFICE
CERTIFICATE OF CORRECTION

PATENT NO. : 4,375,972

DATED : March 8, 1983

INVENTOR(S) : Peter S. Forgione et al.

It is certified that error appears in the above-identified patent and that said Letters Patent are hereby corrected as shown below:

In Formula 2 - Column 3 Line 27

"$Ag - Ag_s$" should read --$Ab - Ag_s$--.

Column 6 - Under Table II insert the following:

-- a

Molar ratio, determined from the amount of free hemoglobin and the amount of hemoglobin in the oligomer fraction as shown by analysis of gel filtration column as in Example I.--.

Signed and Sealed this

Seventeenth Day of May 1983

[SEAL]

Attest:

DONALD J. QUIGG

Attesting Officer

Acting Commissioner of Patents and Trademarks